US00PP25159P3

(12) United States Plant Patent
Schoone

(10) Patent No.: US PP25,159 P3
(45) Date of Patent: Dec. 9, 2014

(54) ***PHALAENOPSIS* ORCHID PLANT NAMED 'FLASHDANCE'**

(50) Latin Name: ***Phalaenopsis* hybrid**
Varietal Denomination: Flashdance

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 101 days.

(21) Appl. No.: 13/573,577

(22) Filed: Sep. 26, 2012

(65) Prior Publication Data

US 2013/0081173 P1 Mar. 28, 2013

Related U.S. Application Data

(60) Provisional application No. 61/540,404, filed on Sep. 28, 2011.

(51) Int. Cl.
*A01H 5/00* (2006.01)
*A01H 5/02* (2006.01)

(52) U.S. Cl.
CPC ..... *A01H 5/02* (2013.01)
USPC ..... Plt./311

(58) Field of Classification Search
USPC ..... Plt./311
See application file for complete search history.

*Primary Examiner* — Annette Para
(74) *Attorney, Agent, or Firm* — Foley & Lardner LLP; Sunit Talapatra

(57) ABSTRACT

A new and distinct *Phalaenopsis* plant named 'Flashdance' particularly characterized by flowers which are purple with a white blush in the center with purple spots; a darker purple labellum with some white and yellow; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Flashdance'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Flashdance'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Flashdance' is a product of a controlled breeding program conducted by the inventors, Rene Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Flashdance' originated from a cross made by the inventor in 1999 in Strengweg, Heemskerk, The Netherlands. The female or seed parent is the *Phalaenopsis* cultivar designated 'Pink Twilight', unpatented. The male or pollen parent is the *Phalaenopsis* cultivar designated '(Spring Moonlight×Sogo Smith)', unpatented. The new *Phalaenopsis* 'Flashdance' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in July, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Flashdance', which in combination distinguish this *Phalaenopsis* as a new and distinct cultivar:

1. flowers which are purple with a white blush in the center with purple spots; a darker purple labellum with some white and yellow;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Flashdance', the female parent 'Pink Twilight' has purple/violet flowers which are about 7.5 cm in size, the male parent '(Spring Moonlight×Sogo Smith)' has light pink colored flowers which are about 10 to 11 cm in size, whereas the flowers of 'Flashdance' are purple/violet with a lighter mark in the center. The flowers of 'Flashdance' are about 8 to 9 cm in size.

Presently, the most commercially similar cultivars to 'Flashdance' are the parent cultivars, to which a comparison is provided above.

BRIEF DESCRIPTION OF THE PHOTOGRAPHS

The accompanying photographs illustrate the overall appearance of the new *Phalaenopsis* 'Flashdance' showing the colors as true as is reasonably possible with colored reproductions of this type. Colors in the photographs may differ slightly from the color values cited in the detailed botanical description, which accurately describe the color of 'Flashdance'.

DETAILED BOTANICAL DESCRIPTION

Figure 1:
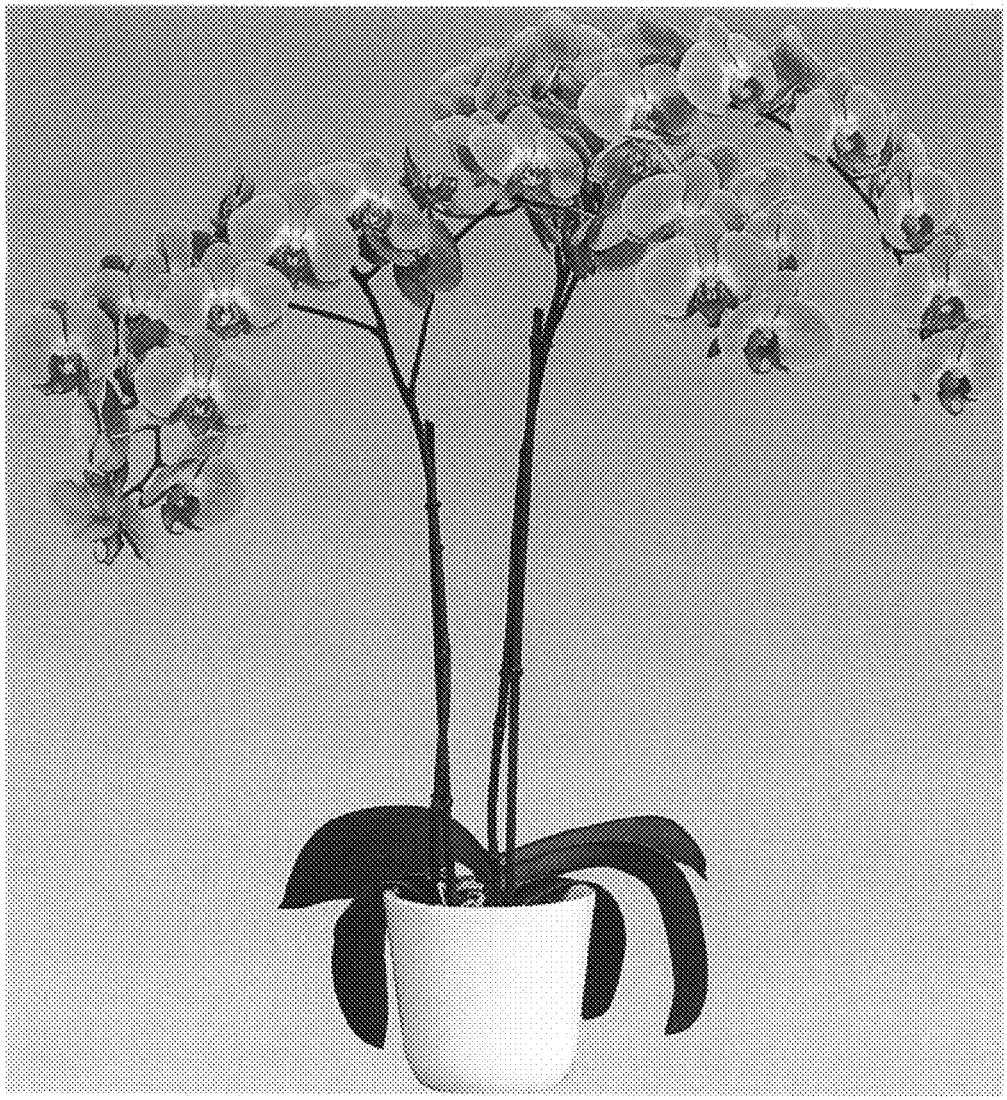
FIG. 1 shows a side view perspective of a typical flowering plant of 'Flashdance' in a 12 cm pot, at 16 months of age.

The new *Phalaenopsis* cultivar 'Flashdance' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Flashdance' as grown in a greenhouse in Strengweg, Heemskerk, The Netherlands, under conditions which closely approximate those generally used in commercial practice. Initially, the ideal temperature to grow plants of 'Flashdance' is 27° C. during the day and at night. Then, during the flowering phase of 'Flashdance', the ideal growing temperature is 20-22° C. during the day and 18° C. at night. Light levels for growing 'Flashdance' are a minimum of 5,000 lux and a maximum of 10,000 lux. A balanced fertilizer with level of 200 ppm N, 87 ppm P, 168 ppm K is applied. Duration of growth of 'Flashdance' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Flashdance' plants described is 12 months after potting.

Classification:

*Botanical.*—*Phalaenopsis* hybrid.

Parentage:

*Female or seed parent.*—*Phalaenopsis* cultivar designated 'Pink Twilight', unpatented.

*Male or pollen parent.*—*Phalaenopsis* cultivar designated '(Spring Moonlight×Sogo Smith)', unpatented.

Propagation:

*Type.*—Tissue culture.

*Rooting habit and description.*—Fleshy; approximately 4 mm-7 mm wide and green/yellow in color (RHS 137D); freely branching. It takes 12 weeks for plants growing in tissue culture to initiate roots.

Plant:

*Size at maturity.*—Height (from bottom of pot to highest flower): about 60 to 70 cm. Spread: about 50 to 70 cm.

*Growth habit.*—Standard; green leaves (RHS N137A) and relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, slightly pointy tip and asymmetric.

*Texture (both surfaces).*—Smooth and leathery.

*Pubescence.*—None.

*Base.*—Acute.

*Margin.*—Entire.

*Mature leaf length.*—About 17 to 25 cm.

*Mature leaf width.*—About 7 to 9 cm.

*Mature leaf thickness.*—About 1 mm.

*Mature leaf color (upper surface).*—RHS N137A.

*Mature leaf color (under surface).*—RHS 143A.

*Venation.*—Pattern: parallel. Color of midvein: upper surface RHS 139A, under surface RHS 143C.

Raceme:

*Quantity per plant.*—About 1 to 2.

*Number of flowers per raceme.*—About 8 to 16.

*Length.*—About 50 to 70 cm.

*Diameter.*—About 4 mm.

*Strength.*—Strong.

*Aspect.*—Upright.

*Texture.*—Glabrous and smooth.

*Color.*—Yellow/green (RHS 147A).

*Internode.*—Length: about 30 to 45 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 18 to 25 mm. Diameter (at midpoint): about 10 to 20 mm. Shape: oval/egg-shaped. Color: RHS N79C.

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
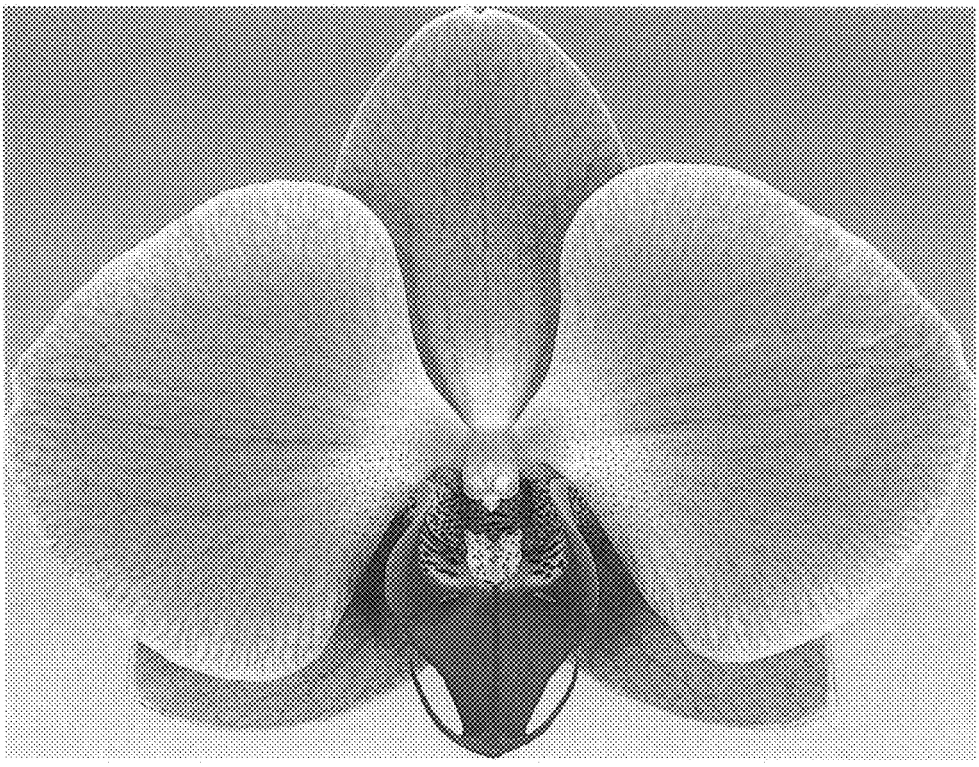
FIG. 2 shows a close-up view of the typical buds and flowers of 'Flashdance'.
Figure 3:
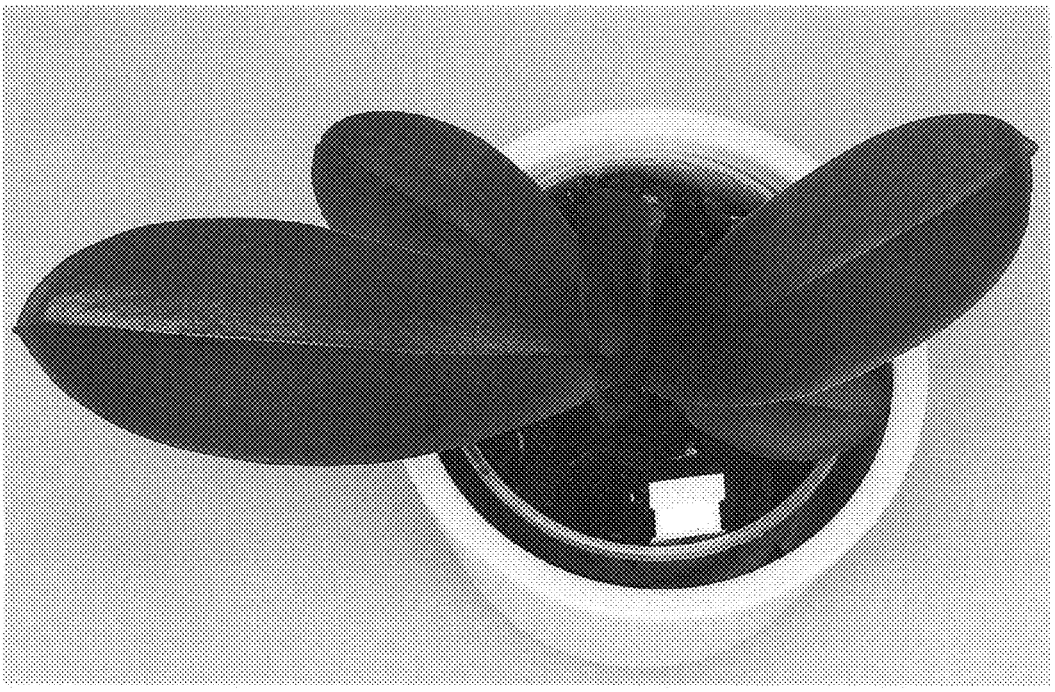
FIG. 3 shows a close-up view of the typical leaves of 'Flashdance'

*Flower*.—Rate of opening: Flowers fully opened about 2 to 3 days after petal and sepal separation. Orientation at opening: slanted upward and outward. Shape: Typical shape of *Phalaenopsis* Orchid; see FIG. 2. Size (of single bloom): Height: about 65 to 80 mm. Diameter: about 80 to 90 mm. Depth of tube: about 15 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and labellum. 2 lateral petals: Overall shape: slightly triangular and weakly cupped. Apex: angular. Margin: entire and weakly undulate. Base: broadly ovate. Length: about 40 to 50 mm. Width: about 35 to 42 mm. Texture: Upper surface: smooth and satiny. Under surface: smooth and satiny. Color (when fully opened): Main color upper surface is RHS N80A. At the base red/purple mark (RHS 69D) with purple/violet (RHS N80A) and purple (RHS N79B) spots. Under surface is purple/violet (RHS N80B). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Length: about 21 mm. Width (not flattened): about 20 mm. Texture: Upper & under surface: smooth and satiny. Color (when fully opened): Main color mid lobe & lateral lobe is RHS 72A. Base and the line in the middle of the mid lobe are slightly darker purple (RHS 186A). Under surface RHS 186A. In the center white (RHS NN155C) with purple spots/stripes (RHS 72A) and on top little yellow and white (RHS 12B). Cirrhi: medium length. Color: purple (RHS 72A). Pestle (Callosities): Length: about 5 mm. Width (not flattened): about 5. Height: about 7 mm. Color: yellow (RHS 7C) with some white (RHS NN155B) and purple stripes/spots (RHS 72A).

*Sepals*.—Arrangement: Outer whorl comprises 3 sepals. Overall shape: elliptical and weakly cupped. Dorsal: at the tip a small triangle-shaped hole. Lateral has slightly pointy tips. Margin: entire and weakly undulate. Length: about 30 to 45 mm. Width: about 27 mm. Apex: oval; dorsal has a small notch. Texture: Upper & under surface: smooth and satiny. Color (when fully opened): Dorsal sepal: thin edge white (RHS NN155D), purple/violet (RSH N80A), red/purple mark at the base (RHS 69D) with purple/violet spots (RHS N80A). Small light purple mark at the base (RHS N78B). Under surface is purple/violet (RHS N80B). Lateral sepal: thin edge green/white (RHSNN155D), purple/violet (RHS N80A), green/white mark at the base (RHS 157C) with small red/purple marks (RHS 71A).

*Pedicel*.—Length: about 30 to 45 mm. Diameter: about 4 mm. Texture: glabrous and smooth. Color: close to flower (RHS 77C) middle (RHS N77B), end (RHS N77A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 10 mm. Diameter: about 7 mm. Color: purple (RHS N78B) with white at the end (RHS 155B).

*Pollinia*.—Quantity: Two. Size: about 1.5 mm. Color: RHS 24A.

*Ovary*.—Length: about 4 mm. Diameter: about 6 mm. Color: RHS NN155C.

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Flashdance', as illustrated and described herein.

* * * * *